(12) United States Patent
Beidler et al.

(10) Patent No.: US 9,688,753 B2
(45) Date of Patent: Jun. 27, 2017

(54) NUCLEIC ACIDS ENCODING ANTIBODIES THAT BIND IL-23

(71) Applicant: Eli Lilly and Company, Indianapolis, IN (US)

(72) Inventors: Catherine Brautigam Beidler, Poway, CA (US); Stuart Willis Bright, Carmel, IN (US); Daniel Scott Girard, San Diego, CA (US); Kristine Kay Kikly, Spiceland, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/702,124

(22) Filed: May 1, 2015

(65) Prior Publication Data

US 2015/0232552 A1 Aug. 20, 2015

Related U.S. Application Data

(62) Division of application No. 14/195,889, filed on Mar. 4, 2014, now Pat. No. 9,023,358.

(60) Provisional application No. 61/774,732, filed on Mar. 8, 13.

(51) Int. Cl.
*C12N 15/13* (2006.01)
*C07K 16/24* (2006.01)
*A61K 39/00* (2006.01)

(52) U.S. Cl.
CPC ...... *C07K 16/244* (2013.01); *A61K 2039/505* (2013.01); *C07K 2317/34* (2013.01); *C07K 2317/56* (2013.01); *C07K 2317/76* (2013.01)

(58) Field of Classification Search
None
See application file for complete search history.

(56) References Cited

U.S. PATENT DOCUMENTS

| | | |
|---|---|---|
| 6,495,667 B1 | 12/2002 | Bazan |
| 7,090,847 B1 | 8/2006 | Oppmann |
| 7,723,485 B2 | 5/2010 | Junutula |
| 7,744,874 B2 | 6/2010 | Korytko |

FOREIGN PATENT DOCUMENTS

| | | |
|---|---|---|
| WO | 2004081190 | 9/2004 |
| WO | 2005052157 | 6/2005 |
| WO | 2006119062 | 11/2006 |
| WO | 2007005955 | 1/2007 |
| WO | 2007024846 | 3/2007 |
| WO | 2007027714 | 3/2007 |
| WO | 2007076524 | 7/2007 |
| WO | 2008103432 | 8/2008 |
| WO | 2012155019 | 11/2012 |

OTHER PUBLICATIONS

Aggarwal, Sudeepta et al.: "Interleukin-23 Promotes a Distinct CD4 T Cell Activation State Characterized by the Production of Interleukin-17", The Journal of Biological Chemistry, vol. 278, No. 3, pp. 1910-1914, Jan. 2003.
Kikly, Kristine et al.: "The IL-23/Th17 axis: Therapeutic targets for autoimmune inflammation", Current Opinion in Immunology, vol. 18, pp. 670-675, 2006.
Langowski, John L. et al.: "IL-23 promotes tumour incidence and growth", Nature Letters, vol. 442, pp. 461-465, Jul. 27, 2006.
Oppmann, Birgit et al.: "Novel p19 Protein Engages IL-12p40 to Form a Cytokine, IL-23, with Biological Activities Similar as Well as Distinct from IL-12", Immunity, vol. 13, pp. 715-725, 2000.
Patent Cooperation Treaty PCT International Search Report from the International Searching Authority dated May 16, 2014 for International Application No. PCT/US14/20064.

*Primary Examiner* — Dong Jiang
(74) *Attorney, Agent, or Firm* — Gregory A. Cox

(57) ABSTRACT

The present invention provides an antibody that binds to the p19 subunit of human IL-23 and is characterized as having high affinity, selective, and neutralizing properties. The antibody is useful in the treatment or prevention of an autoimmune or inflammatory condition selected from the group consisting of consisting of multiple sclerosis, rheumatoid arthritis, psoriasis, inflammatory bowel diseases, ankylosing spondylitis, graft-versus-host disease, lupus and metabolic syndrome. The antibody is also useful in the treatment of cancer.

6 Claims, No Drawings

SEQUENCE LISTING

<160> NUMBER OF SEQ ID NOS: 15

<210> SEQ ID NO 1
<211> LENGTH: 10
<212> TYPE: PRT
<213> ORGANISM: Artificial Sequence

```
<220> FEATURE:
<223> OTHER INFORMATION: synthetic construct

<400> SEQUENCE: 1

Gly Tyr Lys Phe Thr Arg Tyr Val Met His
1               5                   10

<210> SEQ ID NO 2
<211> LENGTH: 17
<212> TYPE: PRT
<213> ORGANISM: Artificial Sequence
<220> FEATURE:
<223> OTHER INFORMATION: synthetic construct

<400> SEQUENCE: 2

Tyr Ile Asn Pro Tyr Asn Asp Gly Thr Asn Tyr Asn Glu Lys Phe Lys
1               5                   10                  15

Gly

<210> SEQ ID NO 3
<211> LENGTH: 8
<212> TYPE: PRT
<213> ORGANISM: Artificial Sequence
<220> FEATURE:
<223> OTHER INFORMATION: synthetic construct

<400> SEQUENCE: 3

Ala Arg Asn Trp Asp Thr Gly Leu
1               5

<210> SEQ ID NO 4
<211> LENGTH: 11
<212> TYPE: PRT
<213> ORGANISM: Artificial Sequence
<220> FEATURE:
<223> OTHER INFORMATION: synthetic construct

<400> SEQUENCE: 4

Lys Ala Ser Asp His Ile Leu Lys Phe Leu Thr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: synthetic construct

<400> SEQUENCE: 5

Gly Ala Thr Ser Leu Glu Thr
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic construct

<400> SEQUENCE: 6

Gln Met Tyr Trp Ser Thr Pro Phe Thr
1               5

<210> SEQ ID NO 7
<211> LENGTH: 115
<212> TYPE: PRT
```

<213> ORGANISM: Artificial Sequence
<220> FEATURE:
<223> OTHER INFORMATION: synthetic construct

<400> SEQUENCE: 7

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Lys Phe Thr Arg Tyr
            20                  25                  30

Val Met His Trp Val Arg Gln Ala Pro Gly Gln Gly Leu Glu Trp Met
        35                  40                  45

Gly Tyr Ile Asn Pro Tyr Asn Asp Gly Thr Asn Tyr Asn Glu Lys Phe
50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Trp Asp Thr Gly Leu Trp Gly Gln Gly Thr Thr Val Thr
            100                 105                 110

Val Ser Ser
        115

<210> SEQ ID NO 8
<211> LENGTH: 107
<212> TYPE: PRT
<213> ORGANISM: Artificial Sequence
<220> FEATURE:
<223> OTHER INFORMATION: synthetic construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Leu Lys Phe
            20                  25                  30

Leu Thr Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Met Tyr Trp Ser Thr Pro Phe
                85                  90                  95

Thr Phe Gly Gly Gly Thr Lys Val Glu Ile Lys
            100                 105

<210> SEQ ID NO 9
<211> LENGTH: 441
<212> TYPE: PRT
<213> ORGANISM: Artificial Sequence
<220> FEATURE:
<223> OTHER INFORMATION: synthetic construct

<400> SEQUENCE: 9

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Lys Phe Thr Arg Tyr
            20                  25                  30

Val Met His Trp Val Arg Gln Ala Pro Gly Gln Gly Leu Glu Trp Met
        35                  40                  45

```
Gly Tyr Ile Asn Pro Tyr Asn Asp Gly Thr Asn Tyr Asn Glu Lys Phe
         50                  55                  60

Lys Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Trp Asp Thr Gly Leu Trp Gly Gln Gly Thr Thr Val Thr
                100                 105                 110

Val Ser Ser Ala Ser Thr Lys Gly Pro Ser Val Phe Pro Leu Ala Pro
            115                 120                 125

Cys Ser Arg Ser Thr Ser Glu Ser Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
    290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
        435                 440

<210> SEQ ID NO 10
<211> LENGTH: 214
```

<212> TYPE: PRT
<213> ORGANISM: Artificial Sequence
<220> FEATURE:
<223> OTHER INFORMATION: synthetic construct

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Asp His Ile Leu Lys Phe
            20                  25                  30

Leu Thr Trp Tyr Gln Gln Lys Pro Gly Lys Ala Pro Lys Leu Leu Ile
        35                  40                  45

Tyr Gly Ala Thr Ser Leu Glu Thr Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Met Tyr Trp Ser Thr Pro Phe
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 11
<211> LENGTH: 345
<212> TYPE: DNA
<213> ORGANISM: Artificial Sequence
<220> FEATURE:
<223> OTHER INFORMATION: synthetic construct

<400> SEQUENCE: 11

```
caggtgcagc tggtgcagtc tggggctgag gtgaagaagc ctgggtcctc ggtgaaggtc    60
tcctgcaagg cttctggata taaattcact cgttatgtta tgcactgggt gcgacaggcc   120
cctggacaag ggcttgagtg gatgggatat attaatcctt acaatgatgg tactaactac   180
aatgagaagt tcaaaggcag agtcacgatt accgcggaca atccacgag cacagcctac   240 atggagctga gcagcctgag atctgaggac acggccgtgt attactgtgc gagaaactgg   300
gacacaggcc tctggggcca aggcaccact gtcacagtct cctca                   345
```

<210> SEQ ID NO 12
<211> LENGTH: 321
<212> TYPE: DNA
<213> ORGANISM: Artificial Sequence
<220> FEATURE:
<223> OTHER INFORMATION: synthetic construct

<400> SEQUENCE: 12

```
gacatccaga tgacccagtc tccatcctcc ctgtctgcat ctgtaggaga cagagtcacc    60
atcacttgca aggcaagtga ccacattctc aaattttttaa cttggtatca gcagaaacca   120
gggaaagccc ctaagctcct gatctatggt gcaaccagtt tggaaactgg ggtcccatca   180
aggttcagtg gcagtggatc tgggacagat ttcactctca ccatcagcag tctgcaacct   240
gaagattttg caacttacta ctgtcaaatg tattggagta ctccgttcac gttcggaggg   300
gggaccaagg tggaaataaa a                                              321
```

<210> SEQ ID NO 13
<211> LENGTH: 1323
<212> TYPE: DNA
<213> ORGANISM: Artificial Sequence
<220> FEATURE:
<223> OTHER INFORMATION: synthetic construct

<400> SEQUENCE: 13

```
caggtgcagc tggtgcagtc tggggctgag gtgaagaagc ctgggtcctc ggtgaaggtc    60
tcctgcaagg cttctggata taaattcact cgttatgtta tgcactgggt gcgacaggcc   120
cctggacaag gcttgagtg gatgggatat attaatcctt acaatgatgg tactaactac   180
aatgagaagt tcaaaggcag agtcacgatt accgcggaca atccacgag cacagcctac   240
atggagctga gcagcctgag atctgaggac acggccgtgt attactgtgc gagaaactgg   300
gacacaggcc tctggggcca aggcaccact gtcacagtct cctcagcctc caccaagggc   360
ccatcggtct tccccgctagc gccctgctcc aggagcacct ccgagagcac agccgccctg   420
ggctgcctgg tcaaggacta cttccccgaa ccggtgacgg tgtcgtggaa ctcaggcgcc   480
ctgaccagcg gcgtgcacac cttcccggct gtcctacagt cctcaggact ctactccctc   540
agcagcgtgg tgaccgtgcc ctccagcagc ttgggcacga agacctacac ctgcaacgta   600
gatcacaagc ccagcaacac caaggtggac aagagagttg agtccaaata tggtccccca   660
tgcccaccct gcccagcacc tgaggccgcc ggggaccat cagtcttcct gttccccccca   720
aaacccaagg acactctcat gatctcccgg acccctgagg tcacgtgcgt ggtggtggac   780
gtgagccagg aagaccccga ggtccagttc aactggtacg tggatggcgt ggaggtgcat   840
aatgccaaga caaagccgcg ggaggagcag ttcaacagca cgtaccgtgt ggtcagcgtc   900
ctcaccgtcc tgcaccagga ctggctgaac ggcaaggagt acaagtgcaa ggtctccaac   960
aaaggcctcc cgtcctccat cgagaaaacc atctccaaag ccaaagggca gccccgagag  1020
ccacaggtgt acaccctgcc cccatcccag gaggagatga ccaagaacca ggtcagcctg  1080
acctgcctgg tcaaaggctt ctaccccagc gacatcgccg tggagtggga aagcaatggg  1140
cagccggaga caactacaa gaccacgcct cccgtgctgg actccgacgg ctccttcttc  1200
ctctacagca ggctaaccgt ggacaagagc aggtggcagg aggggaatgt cttctcatgc  1260
tccgtgatgc atgaggctct gcacaaccac tacacacaga gagcctctc cctgtctctg  1320
ggt                                                                 1323
```

<210> SEQ ID NO 14
<211> LENGTH: 642
<212> TYPE: DNA
<213> ORGANISM: Artificial Sequence
<220> FEATURE:
<223> OTHER INFORMATION: synthetic construct

<400> SEQUENCE: 14

```
gacatccaga tgacccagtc tccatcctcc ctgtctgcat ctgtaggaga cagagtcacc    60
atcacttgca aggcaagtga ccacattctc aaattttaa cttggtatca gcagaaacca   120
gggaaagccc ctaagctcct gatctatggt gcaaccagtt tggaaactgg ggtcccatca   180
aggttcagtg gcagtggatc tgggacagat ttcactctca ccatcagcag tctgcaacct   240
gaagattttg caacttacta ctgtcaaatg tattggagta ctccgttcac gttcggaggg   300
gggaccaagg tggaaataaa acgaactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacctgacg    540 ctgagcaaag cagactacga gaaacacaaa gtctacgcct gcgaagtcac ccatcagggc   600
ctgagctcgc ccgtcacaaa gagcttcaac aggggagagt gc                     642
```

<210> SEQ ID NO 15
<211> LENGTH: 170
<212> TYPE: PRT
<213> ORGANISM: Homo sapiens

<400> SEQUENCE: 15

```
Arg Ala Val Pro Gly Gly Ser Ser Pro Ala Trp Thr Gln Cys Gln Gln
1               5                   10                  15

Leu Ser Gln Lys Leu Cys Thr Leu Ala Trp Ser Ala His Pro Leu Val
            20                  25                  30

Gly His Met Asp Leu Arg Glu Glu Gly Asp Glu Thr Thr Asn Asp
        35                  40                  45

Val Pro His Ile Gln Cys Gly Asp Gly Cys Asp Pro Gln Gly Leu Arg
    50                  55                  60

Asp Asn Ser Gln Phe Cys Leu Gln Arg Ile His Gln Gly Leu Ile Phe
65                  70                  75                  80

Tyr Glu Lys Leu Leu Gly Ser Asp Ile Phe Thr Gly Glu Pro Ser Leu
                85                  90                  95

Leu Pro Asp Ser Pro Val Gly Gln Leu His Ala Ser Leu Leu Gly Leu
            100                 105                 110

Ser Gln Leu Leu Gln Pro Glu Gly His His Trp Glu Thr Gln Gln Ile
        115                 120                 125

Pro Ser Leu Ser Pro Ser Gln Pro Trp Gln Arg Leu Leu Leu Arg Phe
    130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro
                165                 170
```

NUCLEIC ACIDS ENCODING ANTIBODIES THAT BIND IL-23

The present invention relates to antibodies that bind human interleukin-23 (IL-23) and uses thereof.

Interleukin-23 (IL-23) is a disulfide linked heterodimeric cytokine composed of a p19 and p40 subunit. It is part of the interleukin-12 (IL-12) family of cytokines. IL-12 is a heterodimeric cytokine of 70 kDa consisting of covalently linked p40 and p35 subunits. IL-12 plays a critical role in the development of protective innate and adaptive immune responses and in tumour surveillance. IL-12 has also been implicated in the inflammatory response through its capacity to promote T helper type 1 (Th1) responses. However, the functional role of IL-12 in the inflammatory response has been re-evaluated with the discovery of the related cytokine, IL-23. IL-23 is composed of the same p40 subunit as IL-12 but is covalently paired with a p19 subunit. Many of the reagents used to assess the role of IL-12 are directed against the shared IL-12/IL-23 p40 subunit, meaning that the activities previously ascribed to IL-12 may have been mediated via IL-23. The development of IL-23 deficient mice enabled investigators to distinguish between the activities of IL-12 and IL-23 and identified IL-23 as an essential mediator of the autoimmune/inflammatory response.

The functional IL-23 receptor is a heterodimer of the IL-12Rβ1 subunit, which is shared with the IL-12 receptor, and an IL-23R subunit. The receptor for IL-23 is constitutively associated with Janus kinase 2 (Jak2) and predominantly activates STAT3, with less STAT4 activation than IL-12.

The IL-23 receptor is expressed on activated/memory T-cells and natural killer (NK) cells. Monocytes, macrophages and dendritic cells also express IL-23 receptor at low levels. IL-23 supports the differentiation and maintenance of naive CD4+ T-cells into a novel subset of cells called Th17 cells, which are distinct from the classical Th1 and Th2 cells. Th17 cells produce interleukin-17A (IL-17A) and interleukin-17F (IL-17F). Th17 cells produce a range of other factors known to drive inflammatory responses, including tumor necrosis factors known to drive inflammatory responses, including tumor necrosis factor alpha (TNF-α), interleukin-6 (IL-6), granulocyte-macrophage colony-stimulating factor (GM-CSF), CXCL1 and CCL20. NK cells and innate lymphoid cells such as lymphoid tissue induce (LTi)-like cells express IL-23 receptor and retinoic-acid-related orphan receptor (ROR) gamma and produce IL-17 in response to IL-23. IL-1β and IL-23 also co-stimulate gamma-delta T cells to induce IL-17 production without T cell receptor engagement.

There is substantial evidence that IL-23 responsive cells are associated with autoimmune inflammatory diseases and cancer. In particular, an IL-23 specific inhibitor (i.e. an inhibitor that inhibits IL-23 but not IL-12) would be particularly useful as inhibiting IL-23 without affecting IL-12 is hypothesized to maximize therapeutic benefit while minimizing the risk of suppression of host defenses.

Antibodies that specifically bind to the p19 subunit of IL-23 are potentially useful inhibitors, see, for example, WO 2007/024846 and WO 2007/027714. A problem with the antibodies disclosed in WO 2007/024846, at least, is the potential for tissue cross-reactivity, in particular, the potential to bind retinal tissue, which is a safety concern. Furthermore, the antibodies disclosed in WO 2007/024846, at least, have sub-optimal physical-chemical properties, for example, extreme hydrophobicity leading to aggregation, that present a significant barrier to production of the antibodies on an industrial scale. Additionally, no antibody targeting the p19 subunit of IL-23 has been approved for therapeutic use.

Thus, there remains a need for IL-23 antibodies. In particular, there remains a need for IL-23 antibodies that bind with high affinity to the p19 subunit of IL-23, in particular, human IL-23, and do not bind to the p40 subunit of the related cytokine family member, IL-12. More particularly, there remains a need for IL-23 antibodies that bind with high affinity to the p19 subunit of IL-23 and do not observably exhibit tissue cross-reactivity, in particular, retinal tissue cross-reactivity. There is also a need for IL-23 antibodies that possess pharmaceutically acceptable physical-chemical properties that facilitate development, manufacturing or formulation.

The present invention provides an antibody that binds to the p19 subunit of human IL-23 comprising a light chain and a heavy chain, wherein the light chain comprises a light chain variable region (LCVR) and the heavy chain comprises a heavy chain variable region (HCVR), wherein the LCVR comprises amino acid sequences LCDR1, LCDR2, and LCDR3, and the HCVR comprises amino acid sequences HCDR1, HCDR2, and HCDR3, wherein LCDR1 is SEQ ID NO:4, LCDR2 is SEQ ID NO:5, LCDR3 is SEQ ID NO:6, HCDR1 is SEQ ID NO:1, HCDR2 is SEQ ID NO:2, and HCDR3 is SEQ ID NO:3.

In an embodiment of the present invention, the antibody comprises a light chain and a heavy chain, wherein the light chain comprises a light chain variable region (LCVR) and the heavy chain comprises a heavy chain variable region (HCVR), wherein the amino acid sequence of the LCVR is SEQ ID NO: 8 and the amino acid sequence of the HCVR is SEQ ID NO: 7.

In a further embodiment of the present invention, the antibody comprises two light chain variable regions (LCVRs) and two heavy chain variable regions (HCVRs), wherein the amino acid sequence of each LCVR is SEQ ID NO: 8 and the amino acid sequence of each HCVR is SEQ ID NO: 7.

In a still further embodiment of the present invention, the antibody comprises a light chain and a heavy chain, wherein the amino acid sequence of the light chain is SEQ ID NO: 10 and the amino acid sequence of the heavy chain is SEQ ID NO: 9.

In a still further embodiment of the present invention, the antibody comprises two light chains and two heavy chains, wherein the amino acid sequence of each light chain is SEQ ID NO: 10 and the amino acid sequence of each heavy chain is SEQ ID NO: 9.

The present invention provides an antibody that binds to the p19 subunit of human IL-23 comprising a light chain and a heavy chain wherein the light chain comprises a light chain variable region (LCVR) and the heavy chain comprises a heavy chain variable region (HCVR), wherein the LCVR comprises complementarity determining regions LCDR1, LCDR2, and LCDR3, and the HCVR comprises complementarity determining regions HCDR1, HCDR2, and HCDR3, and wherein LCDR1 consists of amino acid sequence SEQ ID NO:4, LCDR2 consists of amino acid sequence SEQ ID NO:5, LCDR3 consists of amino acid sequence SEQ ID NO:6, HCDR1 consists of amino acid sequence SEQ ID NO:1, HCDR2 consists of amino acid sequence SEQ ID NO:2, and HCDR3 consists of amino acid sequence SEQ ID NO:3.

The present invention also provides an antibody that binds to the p19 subunit of human IL-23 comprising a light chain and a heavy chain, wherein the light chain comprises a light chain variable region (LCVR) and the heavy chain comprises a heavy chain variable region (HCVR), wherein the LCVR chain comprises amino acid sequence SEQ ID NO: 8 and the HCVR chain comprises amino acid sequence SEQ ID NO: 7.

The present invention also provides an antibody that binds to the p19 subunit of human IL-23 comprising a light chain and a heavy chain, wherein the light chain comprises amino acid sequence SEQ ID NO: 10 and the heavy chain comprises amino acid sequence SEQ ID NO: 9.

The present invention also provides an antibody that binds to the p19 subunit of human IL-23 comprising two light chains and two heavy chains, wherein each light chain comprises amino acid sequence SEQ ID NO: 10 and each heavy chain comprises amino acid sequence SEQ ID NO: 9.

The amino acid sequences of the antibodies of the present invention are provided below.

| SEQ ID NOs | | | | | |
|---|---|---|---|---|---|
| Antibody | Heavy Chain | Light Chain | HCVR | LCVR | |
| I | 9 | 10 | 7 | 8 | |

| Antibody | HCDR1 | HCDR2 | HCDR3 | LCDR1 | LCDR2 | LCDR3 |
|---|---|---|---|---|---|---|
| I | 1 | 2 | 3 | 4 | 5 | 6 |

The present invention also provides an antibody that binds to the p19 subunit of human IL-23 at a conformational epitope within amino acid positions 81-99 and 115-140 of SEQ ID NO: 15.

The present invention also provides an antibody that binds to the p19 subunit of human IL-23 at a conformational epitope within amino acid positions 81-99 and 115-140 of SEQ ID NO: 15, wherein the antibody contacts at least amino acid residues 94P, 95S, 97L, 98P, 99D, 123W, 130S, 133P and 137W of SEQ ID NO: 15.

In a still further embodiment of the present invention, the antibody is selective to the p19 subunit of human IL-23.

When bound to the p19 subunit of human IL-23, the antibody of the present invention prevents binding of human IL-23 to the IL-23 subunit of the IL-23 receptor. Accordingly, the antibody of the present invention inhibits the activity of human IL-23 at the human IL-23 subunit of the IL-23 receptor.

The antibody of the present invention does not prevent binding of human IL-23 to the IL-12Rβ1 subunit of the IL-23 receptor and, therefore, does not inhibit the activity of human IL-23 at the IL-12Rβ1 subunit of the IL-23 receptor.

The antibody does not detectably bind to the p40 subunit shared by human IL-23 and human IL-12.

In a still further embodiment of the present invention, the antibody the antibody has neutralizing activity to the p19 subunit of human IL-23.

In a still further embodiment of the present invention, the antibody of the present invention has an $IC_{50}$ of less than or equal to about 90 pM. Preferably, the antibody of the present invention has an $IC_{50}$ of less than or equal to about 74 pM. The $IC_{50}$ values are measured in an in vitro murine splenocyte assay as described in the section entitled "In Vitro Neutralization of Human or Cynomolgus Monkey IL-23 by Antibody I in Murine Splenocytes" in Example 1.

In a still further embodiment of the present invention, the antibody of the present invention is selective and has neutralizing activity to the p19 subunit of human IL-23.

In a still further embodiment of the present invention, the antibody of the present invention has a dissociation equilibrium constant, $K_D$, of about 10 pM to about 30 pM for human IL-23. Preferably, the antibody of the present invention has a $K_D$ of about 21 pM for human IL-23. The $K_D$ values are established by binding kinetics at 37° C. as described in the section entitled "Affinity Binding Measurement by Surface Plasmon Resonance (BIAcore for Antibody I" in Example 1. The antibody of the present invention is further characterized with a $k_{on}$ rate to the p19 subunit of human IL-23 of from about $2.2 \times 10^6$ $M^{-1}sec^{-1}$ to about $2.6 \times 10^6$ $M^{-1}$ $sec^{-1}$. Preferably, the antibody of the present invention has a $k_{on}$ rate to the p19 subunit of human IL-23 of about $2.43 \times 10^6$ $M^{-1}sec^{-1}$ The antibody of the present invention is even further characterized with a $k_{off}$ rate to the p19 subunit of human IL-23 of from about $0.30 \times 10^{-4}$ $sec^{-1}$ to about $0.70 \times 10^{-4}$ $sec^{-1}$. Preferably, the antibody of the present invention has a $k_{off}$ rate to the p19 subunit of human IL-23 of about $0.52 \times 10^{-4}$ $sec^{-1}$.

The antibody of the present invention binds to the p19 subunit of human IL-23 with high affinity. For the purposes of the present disclosure, the term "high affinity" refers to a $K_D$ of at least about 21 pM. The $K_D$ values are established by binding kinetics at 37° C. as described in the section entitled "Affinity Binding Measurement by Surface Plasmon Resonance (BIAcore for Antibody I" in Example 1.

Unlike certain prior art antibodies that bind to human IL-23, the antibody of the present invention does not observably exhibit tissue cross-reactivity. In particular, the antibody of the present invention does not observably bind to retinal tissue.

The antibody of the present invention possesses pharmaceutically acceptable physical-chemical properties, including pharmaceutically acceptable solubility in physiological and laboratory conditions, and pharmaceutically acceptable chemical and physical stability wherein the antibody remains in a monomeric form and very little high molecular weight (HMW) aggregates are observed under a range of conditions as described in the section entitled "Physical-Chemical Properties of IL-23 Antibody" in Example 1.

The present invention further provides pharmaceutical compositions comprising an antibody of the present invention and one or more pharmaceutically acceptable carriers, diluents or excipients. More particularly, the pharmaceutical compositions of the present invention further comprise one or more additional therapeutic agents.

The present invention also provides a method of treating or preventing a condition in a patient, comprising administering to a patient in need thereof an effective amount of an antibody of the present invention, wherein the condition is an autoimmune or inflammatory condition selected from the group consisting of multiple sclerosis, rheumatoid arthritis, psoriasis, inflammatory bowel diseases, ankylosing spondylitis, graft-versus-host disease, lupus and metabolic syndrome.

The present invention also provides a method of treating or preventing a condition in a patient, comprising administering to a patient in need thereof an effective amount of an antibody of the present invention, wherein the condition is cancer.

In an embodiment of the present invention, the cancer is melanoma, colon, ovarian, head and neck, lung, breast, or stomach cancer.

The present invention also provides the antibody of the present invention for use in therapy.

More particularly, the present invention provides the antibody of the present invention for use in the treatment or prevention of an autoimmune or inflammatory condition selected from the group consisting of multiple sclerosis, rheumatoid arthritis, psoriasis, inflammatory bowel diseases, ankylosing spondylitis, graft-versus-host disease, lupus and metabolic syndrome.

The present invention also provides the antibody of the present invention for use in the treatment or prevention of cancer.

In an embodiment of the present invention, the cancer is melanoma, colon, ovarian, head and neck, lung, breast, or stomach cancer. The present invention provides the use of an antibody of the present invention in the manufacture of a medicament for the treatment or prevention of a condition selected from the group consisting of multiple sclerosis, rheumatoid arthritis, psoriasis, inflammatory bowel diseases, ankylosing spondylitis, graft-versus-host disease, lupus and metabolic syndrome.

The present invention also provides the use of an antibody of the present invention in the manufacture of a medicament for the treatment or prevention of cancer.

In an embodiment of the present invention, the cancer is melanoma, colon, ovarian, head and neck, lung, breast, or stomach cancer.

The present invention also relates to polynucleotides encoding the above-described antibody of the present invention.

The present invention provides a DNA molecule comprising a polynucleotide sequence encoding a light chain polypeptide having the amino acid sequence SEQ ID NO: 10.

The present invention also provides a DNA molecule comprising a polynucleotide sequence encoding a heavy chain polypeptide having the amino acid sequence SEQ ID NO: 9.

In one embodiment, the present invention provides a polynucleotide encoding an antibody of the present invention, wherein the HCVR is encoded by SEQ ID NO: 11 and the LCVR is encoded by SEQ ID NO: 12.

In a further embodiment, the present invention provides a polynucleotide encoding an antibody of the present invention, wherein the heavy chain is encoded by SEQ ID NO: 13 and the light chain is encoded by SEQ ID NO: 14.

The polynucleotides of the present invention may be in the form of RNA or in the form of DNA, which DNA includes cDNA, and synthetic DNA. The DNA may be double-stranded or single-stranded. The coding sequences that encode the antibody of the present invention may vary as a result of the redundancy or degeneracy of the genetic code.

The polynucleotides that encode for the antibody of the present invention may include the following: only the coding sequence for the antibody, the coding sequence for the antibody and an additional coding sequence such as a leader or secretory sequence or a pro-protein sequence; the coding sequence for the antibody and non-coding sequence, such as introns or non-coding sequence 5' and/or 3' of the coding sequence for the protein. Thus the term "polynucleotide encoding an antibody" encompasses a polynucleotide that may include not only coding sequence for the protein but also a polynucleotide that includes additional coding and/or non-coding sequence.

The polynucleotides of the present invention will be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The present invention provides a recombinant host cell comprising the DNA molecule of comprising a polynucleotide sequence encoding a light chain polypeptide having the amino acid sequence SEQ ID NO: 10 and the DNA molecule comprising a polynucleotide sequence encoding a heavy chain polypeptide having the amino acid sequence SEQ ID NO: 9, which cell is capable of expressing an antibody comprising a heavy chain and a light chain, wherein the amino acid sequence of the heavy chain is SEQ ID NO: 9 and the amino acid sequence of the light chain is SEQ ID NO: 10.

The antibody of the present invention may readily be produced in mammalian cells such as CHO, NS0, HEK293 or COS cells; in bacterial cells such as *E. coli, Bacillus subtilis*, or *Pseudomonas fluorescence*; or in fungal or yeast cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host. For example, calcium chloride transformation is commonly utilized for prokaryotic cells, whereas calcium phosphate treatment or electroporation may be used for other cellular hosts.

Various methods of protein purification may be employed and such methods are known in the art and described, for example, in Deutscher, *Methods in Enzymology* 182: 83-89 (1990) and Scopes, *Protein Purification: Principles and Practice*, 3rd Edition, Springer, N.Y. (1994).

The present invention provides a process for producing an antibody that binds to the p19 subunit of human IL-23 comprising a heavy chain and a light chain, wherein the heavy chain comprises amino acid sequence SEQ ID NO: 9 and light chain comprise amino acid sequences SEQ ID NO: 10, said process comprising the steps of:
 a) cultivating a recombinant host cell of claim 7 under conditions such that said antibody is expressed; and
 b) recovering from said host cell the expressed antibody.

Further, the present invention provides a process for producing an antibody that binds to the p19 subunit of human IL-23 having a heavy chain and a light chain, wherein the amino acid sequence of the heavy chain is SEQ ID NO: 9 and the amino acid sequence of the light chain is SEQ ID NO: 10, said process comprising the steps of:
 a) cultivating a recombinant host cell comprising a first polynucleotide sequence encoding the polypeptide sequence given by SEQ ID NO: 9 and a second polynucleotide sequence encoding the polypeptide sequence given by SEQ ID NO: 10, under conditions such that said polypeptide sequences are expressed; and
 b) recovering from said host cell an antibody comprising a heavy chain and a light chain, wherein the polypeptide sequence of said heavy chain is given by SEQ ID NO: 9 and the polypeptide sequence of said light chain is given by SEQ ID NO: 10.

In one embodiment of the above-described process, the first polynucleotide sequence encoding the polypeptide sequence given by SEQ ID NO: 9 and the second polynucleotide sequence encoding the polypeptide sequence given by SEQ ID NO: 10 are part of the same nucleic acid molecule.

In an embodiment, the present invention provides an antibody produced by the afore-mentioned process.

In a further embodiment, the antibody produced by the afore-mentioned process has two heavy chains and two light chains, wherein the polypeptide sequence of each heavy chain is given by SEQ ID NO: 9 and the polypeptide sequence of each light chain is given by SEQ ID NO: 10.

The antibody of the present invention is an IgG type antibody and has four amino acid chains (two "heavy" chains and two "light" chains) that are cross-linked via intra- and inter-chain disulfide bonds. When expressed in certain biological systems, antibodies having native human Fc sequences are glycosylated in the Fc region. Antibodies may be glycosylated at other positions as well.

Each heavy chain is comprised of an N-terminal HCVR and a heavy chain constant region ("HCCR"). Human heavy chains are classified as gamma, mu, alpha, delta, or epsilon, and define the isotype of an antibody as IgG, IgM, IgA, IgD, or IgE, respectively. Human IgG antibodies can be further divided into subclasses, e.g., $IgG_1$, $IgG_2$, $IgG_3$, $IgG_4$.

Preferably, the antibody of the present invention contains an Fc portion which is derived from human $IgG_4$ Fc region because of a reduced ability to engage Fc receptor-mediated inflammatory mechanisms or to activate complement resulting in reduced effector function.

More preferably, the antibody of the present invention contains an $IgG_4$-PAA Fc portion. The $IgG_4$-PAA Fc portion has a serine to proline mutation at position 223 (S223P; SEQ ID NO: 9), a phenylalanine to alanine mutation at position 229 (F229A; SEQ ID NO: 9) and a leucine to alanine mutation at position 230 (L230A; SEQ ID NO: 9). The S223P mutation is a hinge mutation that prevents half-antibody formation (phenomenon of dynamic exchange of half-molecules in $IgG_4$ antibodies). The F229A and L230A mutations further reduce effector function of the already low human $IgG_4$ isotype.

Each heavy chain type is also characterized by a particular constant region with a sequence well known in the art. The heavy chain constant region is comprised of three domains (CH1, CH2, and CH3) for IgG.

Light chains are classified as kappa or lambda, which are each characterized by a particular constant region as known in the art. Each light chain is comprised of a LCVR and a light chain constant region ("LCCR"). Preferably, the antibody of the present invention comprises a kappa light chain.

The variable regions of each light/heavy chain pair form the antibody binding site. The HCVR and LCVR regions can be further subdivided into regions of hyper-variability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen. There are currently three systems of CDR assignments for antibodies that are used for sequence delineation. The Kabat CDR definition (Kabat et al., "Sequences of Proteins of Immunological Interest," National Institutes of Health, Bethesda, Md. (1991)) is based upon antibody sequence variability. The Chothia CDR definition (Chothia et al., "Canonical structures for the hyper-variable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)) is based on three-dimensional structures of antibodies and topologies of the CDR loops. The Chothia CDR definitions are identical to the Kabat CDR definitions with the exception of HCDR1 and HCDR2. The North CDR definition (North et al., "A New Clustering of Antibody CDR Loop Conformations", Journal of Molecular Biology, 406, 228-256 (2011)) is based on affinity propagation clustering with a large number of crystal structures.

For the purposes of the present invention, a consensus of the three methods is used to define CDRs. In the case of the light chain CDRs, the Kabat and Chothia CDR definitions are used. In the case of HCDR1, a hybrid of the Kabat and Chothia CDR definitions is used. The Kabat definition of HCDR1 starts eight residues after the first cysteine of the heavy chain and is five residues in length, whereas the Chothia definition of HCDR1 starts three residues after this cysteine and is seven residues in length. The HCDR1 of the antibody of the present invention is defined by the Chothia starting position and the Kabat end position. In the case of HCDR2, the Kabat CDR definition is used. In the case of HCDR3, a hybrid of the North, Kabat and Chothia CDR definitions is used. The Kabat definition of HCDR3 comprises residues 95-102 of the heavy chain (SEQ ID NO: 13 for the antibody of the present invention) and typically starts three residues after a cysteine. The Chothia definition of HCDR3 is the same as the Kabat definition. The North definition of HCDR3 comprises residues 93-102 of the heavy chain (SEQ ID NO: 13 for the antibody of the present invention) and typically starts immediately after the cysteine residue. The HCDR3 of the antibody of the present invention is defined by the North starting position and the Kabat/Chothia/North end position.

Table 1 shows exemplary CDR assignments of the antibody of the present invention.

TABLE 1

CDR Assignments

| CDR | Start Definition | End Definition |
|---|---|---|
| LCDR1 | Kabat/Chothia/North | Kabat/Chothia/North |
| LCDR2 | Kabat/Chothia | Kabat/Chothia/North |
| LCDR3 | Kabat/Chothia/North | Kabat/Chothia/North |
| HCDR1 | Chothia | Kabat/North |
| HCDR2 | Kabat/North | Kabat |
| HCDR3 | North | Kabat/Chothia/North |

An antibody of the present invention is an engineered antibody that has been designed to have frameworks, hinge regions, and constant regions of human origin that are identical with or substantially identical (substantially human) with frameworks and constant regions derived from human genomic sequences. Fully human frameworks, hinge regions, and constant regions are those human germline sequences as well as sequences with naturally-occurring somatic mutations and those with engineered mutations. An antibody of the present invention may comprise framework, hinge, or constant regions derived from a fully human framework, hinge, or constant region containing one or more amino acid substitutions, deletions, or additions therein. Further, an antibody of the present invention is preferably substantially non-immunogenic in humans.

A variety of different human framework sequences may be used singly or in combination as a basis for an antibody of the present invention. Preferably, the framework regions of an antibody of the present invention are of human origin or substantially human (at least 95%, 97% or 99% of human origin.) The sequences of framework regions of human origin may be obtained from The Immunoglobulin Factsbook, by Marie-Paule Lafranc, Gerard Lefranc, Academic Press 2001, ISBN 012441351.

The framework sequence for an antibody of the present invention serves as the "donor" variable framework region and can be used to create additional antibodies with the same CDRs specified herein using methodology known in the art. Furthermore, the framework sequence for an antibody of the present invention can be compared to other known human framework sequences to generate additional antibodies. Thus, this information can be used to "back-mutate" another selected homologous human framework region to the donor amino acid residue at these positions. Further, any "rare" amino acids can be detected in additional human frameworks such that the consensus or donor amino acid residue can be used at the relevant position.

Methods for producing and purifying antibodies are well known in the art and can be found, for example, in Harlow and Lane (1988) *Antibodies. A Laboratory Manual*, Cold Spring Harbor Laboratory Press. Cold Spring Harbor, New York, Chapters 5-8 and 15. For example, mice can be immunized with human IL-23, or fragments thereof, and the resulting antibodies can then be recovered, purified and the amino acid sequences determined using conventional methods well known in the art. The antibody of the present invention is engineered to contain one or more human framework regions surrounding CDRs derived from a non-human antibody. Human framework germline sequences can be obtained from ImMunoGeneTics (IMGT) via their website http://imgt.cines.fr, or from *The Immunoglobulin Facts Book* by Marie-Paule Lefranc and Gerard Lefranc, Academic Press, 2001, ISBN 012441351. Particular, germline light chain frameworks for use in the antibody of the present invention include 02.

Particular germline heavy chain framework regions for use in the antibody of the present invention include VH1-69.

The engineered antibodies of the present invention may be prepared and purified using known methods. For example, cDNA sequences encoding a heavy chain (for example, the amino acid sequence given by SEQ ID NO: 9) and a light chain (for example, the amino acid sequence given by SEQ ID NO: 10) may be cloned and engineered into a GS (glutamine synthetase) expression vector. The engineered immunoglobulin expression vector may then be stably transfected in CHO cells. Mammalian expression of antibodies will result in glycosylation, typically at highly conserved N-glycosylation sites in the Fc region. Stable clones may be verified for expression of an antibody specifically binding to human IL-23. Positive clones may be expanded into serum-free culture medium for antibody production in bioreactors. Media, into which an antibody has been secreted, may be purified by conventional techniques. For example, the medium may be conveniently applied to a Protein A or G Sepharose FF column that has been equilibrated with a compatible buffer, such as phosphate buffered saline. The column is washed to remove nonspecific binding components. The bound antibody is eluted, for example, by pH gradient and antibody fractions are detected, such as by SDS-PAGE, and then pooled. The antibody may be concentrated and/or sterile filtered using common techniques. Soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

The antibodies of the present invention are monoclonal antibodies. "Monoclonal antibody" or "mAb", as used herein, refers to an antibody that is derived from a single copy or clone including, for example, any eukaryotic, prokaryotic, or phage clone, and not the method by which it is produced. Monoclonal antibodies thereof can be produced, for example, by hybridoma technologies, recombinant technologies, phage display technologies, synthetic technologies, e.g., CDR-grafting, or combinations of such or other technologies known in the art.

In another embodiment of the present invention, the antibody, or the nucleic acid encoding the same, is provided in isolated form.

The antibody of the present invention, or pharmaceutical compositions comprising the same, may be administered by parenteral routes (e.g., subcutaneous, intravenous, intraperitoneal, intramuscular, or transdermal).

Pharmaceutical compositions of the present invention can be prepared by methods well known in the art (e.g., *Remington: The Science and Practice a/Pharmacy,* $19^{th}$ edition (1995), (A. Gennaro et al., Mack Publishing Co.) and comprise an antibody as disclosed herein, and one or more pharmaceutically acceptable carriers, diluents, or excipients. For example, an antibody of the present invention can be formulated with agents such as sodium citrate, citric acid, polysorbate 80, sodium chloride and sucrose and the resulting composition may then be lyophilized and stored at 2° C.-8° C. The lyophilized composition may then be reconstituted with sterile water for injection prior to administration.

The term "bind (or "binds") to the p19 subunit of human IL-23", as used herein, refers to a detectable interaction of the antibody of the present invention with an epitope on the p19 subunit of human IL-23 given by the amino acid sequence of SEQ ID NO: 15. The interaction between the antibody of the present invention and the p19 subunit of human IL-23 is measured by binding kinetics at 37° C. as described in the section entitled "Affinity Binding Measurement by Surface Plasmon Resonance (BIAcore) for Antibody I" in Example 1.

The term "epitope" as used herein refers to amino acid residues that lie close together on the protein (antigen) surface and interact with an antibody. There are two broad classes of epitopes: linear epitopes and conformational epitopes.

The term "linear epitope" as used herein refers to a continuous primary amino acid sequence of a particular region of a protein.

The term "conformational epitope" as used herein refers to discontinuous sections of the antigen's amino acid sequence that are contacted by the antibody of the invention. Conformational epitopes are defined by the structure as well as the sequence of the native protein; these epitopes may be continuous or discontinuous. Components of the epitope can be situated on disparate parts of the protein, which are brought close to each other in the folded native protein structure. In the context of the present invention, the antibody of the present invention binds to a conformational epitope within amino acid positions 81-99 and 115-140 of SEQ ID NO: 15, wherein the antibody contacts at least amino acids residues 94P, 95S, 97L, 98P, 99D, 123W, 130S, 133P and 137W of SEQ ID NO: 15. The conformational epitope is not, however, limited to these amino acid residues and may comprise additional amino acid residues within amino acid positions 81-99 and 115-140 of SEQ ID NO: 15.

The term "does not observably bind retinal tissue", as used herein, refers to the absence of a detectable interaction of the antibody of the present invention with human and cynomolgus monkey retinal tissue. The interaction between the antibody of the present invention and the human and cynomolgus monkey retinal tissue is assessed in an immunohistochemistry assay as described in the section entitled "Retinal Tissue Cross-Reactivity: In Vitro Analysis by Immunohistochemistry" in Example 1. The term "observably" as used in the present context refers to a visual assessment of the human and cynomolgus monkey retinal tissue to determine if the antibody of the present invention binds to said human and cynomolgus monkey retinal tissue.

The term "selective" as used herein in reference to an antibody of the present invention refers to an antibody that binds the p19 subunit of human IL-23 but does not bind to the p40 subunit shared by human IL-23 and human IL-12.

The term "neutralizing" refers to "neutralizing antibody", as used herein, is intended to refer to inhibition of the biological activity of human IL-23. Measuring one or more indicators of IL-23 biological activity as determined using either the mouse splenocyte bioassay (see section entitled "In Vitro Neutralization of Human or Cynomolgus Monkey IL-23 by Antibody I in Murine Splenocytes in Example 1) or the human IL-23 neutralization assay (see section entitled "Neutralization of Human IL-23: Acute, Local" in Example 1) can assess this inhibition of the biological activity of human IL-23.

The term "$K_D$", as used herein, is intended to refer to the dissociation constant of a particular antibody-antigen interaction. It is calculated by the formula:

$$K_{off}/K_{on} = K_D$$

The term "$k_{on}$", as used herein, is intended to refer to the association or on rate constant, or specific reaction rate, of the forward, or complex-forming, reaction, measured in units: $M^{-1}sec^{-1}$.

The term "$k_{off}$", as used herein, is intended to refer to the dissociation or off rate constant, or specific reaction rate, for dissociation of an antibody from the antibody/antigen complex, measured in units: $sec^{-1}$.

The term "$IC_{50}$", as used herein, is intended to refer to the effective concentration of antibody of the present invention needed to neutralize 50% of the bioactivity of IL-23 on mouse splenocytes in the bioassay described in the section entitled "In Vitro Neutralization of Human or Cynomolgus Monkey IL-23 by Antibody I in Murine Splenocytes in Example 1.

The term "polynucleotide", as used herein, is intended to include DNA molecules and RNA molecules. A nucleic acid molecule may be single-stranded or double-stranded.

The term "isolated", as used herein, refers to a protein, peptide or nucleic acid which is free or substantially free from other macromolecular species found in a cellular environment.

The term "substantially free", as used herein, means the protein, peptide or nucleic acid of interest comprises more than 80% (on a molar basis) of the macromolecular species present, preferably more than 90% and more preferably more than 95%.

A "patient" is a mammal, preferably a human.

The term "treating" (or "treat" or "treatment") refers to slowing, interrupting, arresting, alleviating, stopping, reducing, or reversing the progression or severity of an existing symptom, disorder, condition, or disease The term "effective amount", as used herein, refers to the amount or dose of an antibody of the present invention which, upon single or multiple dose administration to the patient, provides the desired effect in the patient under treatment. An effective amount can be readily determined by the attending diagnostician, as one skilled in the art, by considering a number of factors such as the species of mammal; its size, age, and general health; the specific disease involved; the degree or severity of the disease; the response of the individual patient; the particular antibody administered; the mode of administration; the bioavailability characteristics of the preparation administered; the dose regimen selected; and the use of any concomitant medications.

EXAMPLE

The following Example further illustrates the invention. It is understood, however, that the Example is set forth by way of illustration and not limitation, and that various modifications may be made by one of ordinary skill in the art.

Example 1

Production of Antibodies

Antibody I of this example comprises two heavy chains and two light chains, each heavy chain having the amino acid sequence given by SEQ ID NO: 9 and each light chain having the amino acid sequence given by SEQ ID NO: 10. Antibody I can be made and purified as follows. An appropriate host cell, such as HEK 293 or CHO, is either transiently or stably transfected with an expression system for secreting antibodies using an optimal predetermined HC:LC vector ratio or a single vector system encoding both heavy chain (SEQ ID NO: 9) and light chain (SEQ ID NO: 10). Clarified media, into which the antibody has been secreted, is purified using any of many commonly-used techniques. For example, the medium may be conveniently applied to a Protein A or G column that has been equilibrated with a compatible buffer, such as phosphate buffered saline (pH 7.4). The column is washed to remove nonspecific binding components. The bound antibody is eluted, for example, by pH gradient (such as 0.1 M sodium phosphate buffer pH 6.8 to 0.1 M sodium citrate buffer pH 2.5). Antibody fractions are neutralized (for example by adding $\frac{1}{10}^{th}$ volume of 1M TRIS at pH 8.0), detected, such as by SDS-PAGE, and then are pooled. Further purification is optional, depending on the intended use. The antibody may be concentrated and/or sterile filtered using common techniques. Soluble aggregate and multimers may be effectively removed by common techniques, including size exclusion, hydrophobic interaction, ion exchange, or hydroxyapatite chromatography. The purity of the antibody after these chromatography steps is greater than 99%. The product may be immediately frozen at −70° C. or may be lyophilized.

Affinity Binding Measurement by Surface Plasmon Resonance (BIAcore)

Antibody affinity ($K_D$) to human, cynomolgus monkey or rabbit IL-23 is determined using a BIAcore Biosensor 2000 and BIAevaluation software with a 1:1 binding with mass transfer model. A capture protein (Protein A, Calbiochem) is coupled via free amine groups to carboxyl groups on flow cells 1 and 2 of a CM4 biosensor chip using a mixture of N-ethyl-N-(dimethylaminopropyl)-carbodiimide (EDC) and N-hydroxysuccinimide (NHS). Flow cells are monitored with a flow rate of 80 µL/minute using a buffer containing 0.01 M HEPES, pH 7.4, 150 mM NaCl, 0.005% surfactant P20. Antibody I is captured on flow cell 2 to yield a total of 40 to 60 response units (RU). Multiple cycles of increasing concentrations of IL-23 are then injected over flow cells 1 and 2 (0.62 nM to 30 nM for human and monkey IL-23 and 30 nM to 240 nM for rabbit IL-23) followed by a regeneration step using glycine-HCl (pH 1.5) between each cycle. Flow cell 1 is used as a control to monitor non-specific binding of IL-23 and the data reflects flow cell 2 minus flow cell 1. Each cycle includes an antibody capture step followed by injection of IL-23 at one concentration with a 30 minute dissociation period, then regeneration. Two cycles where buffer is injected in place of IL-23, serve as a control for baseline subtraction and correct for drift associated with the dissociation of Antibody I from the protein A surface. Affinity is measured at 37° C. The assay is performed 2 times with human, monkey or rabbit IL-23. Antibody I is tested 2 times each with mouse IL-23 at 333 nM, rat IL-23 at 200 nM, human IL-12 at 333 nM, human IL-27 at 500 nM or human IL-35 at 833 nM.

The on-rate ($k_{on}$) and off-rate ($k_{off}$) for each antigen are evaluated using a 1:1 binding with mass transfer model. The affinity ($K_D$) is calculated from the binding kinetics according to the relationship: $K_D = k_{off}/k_{on}$.

TABLE 2

Binding Parameters for Antibody I

| Antigen | On Rate ($k_{on}$) (Avg ± SD) ($M^{-1}s^{-1}$) ($10^6$) | Off Rate ($k_{off}$) (Avg ± SD) ($s^{-1}$) ($10^{-4}$) | Affinity ($K_D{}^a$) (Avg ± SD) (pM) |
|---|---|---|---|
| Human IL-12 | No detectable binding | No detectable binding | No detectable binding |
| Human IL-23 | 2.43 ± 0.16 | 0.52 ± 0.21 | 21 ± 9.9 |
| Human IL-27 | No detectable binding | No detectable binding | No detectable binding |
| Human IL-35 | No detectable binding | No detectable binding | No detectable binding |
| Monkey IL-23 | 1.28 ± 0.05 | 0.7 ± 0.11 | 55 ± 6.4 |
| Rabbit IL-23 | 0.09 ± 0.001 | 47.9 ± 0.4 | 53,000 ± 1131 |
| Mouse IL-23 | No detectable binding | No detectable binding | No detectable binding |
| Rat IL-23 | No detectable binding | No detectable binding | No detectable binding |

$^a$Calculated as $K_D = k_{off}/k_{on}$
n = 2 for each antigen. IL-12 was tested at a 400× concentration of what is detectable for IL-23. IL-27 and IL-35 were tested at an 800× concentration of what is detectable for IL-23. Mouse and rat IL-23 were tested at 500× and 300× concentrations of what is detectable for human IL-23.

Antibody I produces a concentration-dependent binding response with human, cynomolgus monkey, and rabbit IL-23 using this method. Saturation of binding of IL-23 is attained at a concentration of 30 nM (human and monkey) and 240 nM (rabbit) using 80-100 response units of Antibody I captured on the chip surface. Under the conditions tested, the binding affinity ($K_D$) of human, monkey, or rabbit IL-23 to Antibody I is 21, 55 or 53,000 pM respectively (Table 1). Mouse IL-23, rat IL-23, human IL-12, human IL-27 or human IL-35 do not bind to Antibody I under these conditions.

In Vitro Inhibition of IL-23 Binding to IL-23 Receptor

Recombinant human IL-23R/Fc is coupled via free amine groups to carboxyl groups on flow cell 2 of a CM4 biosensor chip using a mixture of N-ethyl-N-(dimethylaminopropyl)-carbodiimide (EDC) and N-hydroxysuccinimide (NHS). Recombinant human $IgG_1$ Fc (R&D Systems, Inc.) is coupled using the same method to flow cell 1 of the same chip. Mouse anti-6×HIS antibody (R&D Systems, Inc.) is coupled using the same method to flow cell 4 of the same chip. Mouse anti-6×HIS is used to pre-capture human IL-12Rβ1/Fc (R&D Systems, Inc.) which contains a HIS tag. Flow cells are monitored with a flow rate of 30 μL/minute using a buffer containing 0.01 M HEPES, pH 7.4, 150 mM NaCl, 0.005% surfactant P20. Recombinant human IL-23 is pre-incubated for 90 minutes with or without the addition of a 16× molar excess of Antibody I. Each combination is injected over flow cells 1, 2 and 4 in a total volume of 150 μL followed by a regeneration step using glycine-HCl (pH 1.5) between each test. Flow cell 1 is used as a control to monitor non-specific binding of IL-23 to the chip. BIAevaluation software is used to prepare overlays of individual binding sensorgrams.

Antibody I neutralizes human IL-23 using in vitro functional assays. Furthermore, Antibody I prevents binding of IL-23 to IL-23R/Fc. The data in Table 3 shows:

(A) IL-23 binds to IL-23R/Fc;
(B) Antibody I/IL-23 complex does not bind to IL-23R/Fc;
(C) IL-23 binds to IL-12Rβ1/Fc; and
(D) Antibody I/IL-23 complex binds to IL-12Rβ1/Fc.

TABLE 3

Effect of Antibody I on IL-23 binding to IL-23R

| Cytokine | Antibody | Binding to IL-23R | Binding to IL-12Rβ1 |
|---|---|---|---|
| IL-23 | None | YES | YES |
| IL-23 | I | NO | YES |

Thus, Antibody I neutralizes IL-23 because it inhibits the binding of IL-23 to the IL-23R subunit. Additionally, Antibody I does not inhibit binding of IL-23 to the IL-12Rβ1 subunit.

In Vitro Neutralization of Human or Cynomolgus Monkey IL-23 by Antibody I in Murine Splenocytes For evaluation of Antibody I, a concentration of human or cynomolgus monkey IL-23 that gives approximately 50% of maximal production of IL-17 is used (16 pM). A dose response ranging from 800,000 to 4.4 pM of Antibody I is evaluated. Antibody I or an $IgG_4$ control antibody is combined with human or cynomolgus monkey IL-23 in a separate well for 90 minutes at 37° C. before addition to the cells (pre-incubation mix).

Splenocytes from C57BL/6 mice stimulated with IL-23 and IL-2 produce IL-17 (Aggarwal, S. et al., "Interleukin-23 Promotes a Distinct CD4 T Cell Activation State Characterized by the Production of Interleukin-17", Journal of Biological Chemistry, 278 (3): 1910-1914 2003). Mouse splenocytes are re-suspended at $5×10^6$ WBC/mL in assay media (RPMI1640 with L-glutamine containing 10% FBS, 1% non-essential amino acids, 1 mM sodium pyruvate, 100 U/mL penicillin, 100 μg/ml streptomycin, 0.00035% 2-mercaptoethanol, 50 ng/mL human IL-2) and dispensed in volumes of 100 μL per well into a 96-well culture plate. The pre-incubation mix of Antibody I/IL-23 is dispensed as 100 μL per well and incubated at 37° C. in 5% $CO_2$. Forty-eight hours later, culture supernatants are tested for mIL-17 using a commercial ELISA kit from R&D Systems (DY421)

according to the instructions in the kit using duplicate wells at each dilution. An $IC_{50}$ is determined using a 4 parameter curve fit of the data.

Mouse splenocytes produce IL-17 in response to human or cynomolgus monkey IL-23. Antibody I neutralizes human or cynomolgus monkey IL-23. The calculated $IC_{50}$ is 82±11 pM for human and 120±14 pM for cynomolgus monkey IL-23, n=2 for each (Table 4). These results demonstrate that Antibody I is able to neutralize human or cynomolgus monkey IL-23 in vitro.

TABLE 4

$IC_{50}$ in the in vitro human and cynomolgus monkey IL-23 neutralization assay

| Species | Assay # | Antibody | $IC_{50}$ (pM) |
|---|---|---|---|
| Human | 1 | I | 90 |
| Human | 2 | I | 74 |
| Human | | Average (SD) | 82 (11) |
| Cyno | 3 | I | 110 |
| Cyno | 4 | I | 130 |
| Cyno | | Average (SD) | 120 (14) |

Neutralization of Human IL-23: Acute, Local

Animals (C57BL/six females, eight weeks old from Jackson Labs) are housed (minimum of 72 hrs after arrival) and fed normally prior to the experiment and for the duration of the study. Hair is removed from the back of mice with electric clippers, and 3 days later mice (n=10 per group) received a subcutaneous injection of Antibody I or an $IgG_4$ isotype control antibody (0.54 mg per mouse). The following 2 days, mice are injected intradermally with human IL-23 in one location on one side of the back (1 μg in 50 μL diluted with sterile saline) using a 29-gauge needle. Sterile saline is used as a vehicle control on the other side of the back. Mice are sacrificed 24 hours after the last human IL-23 injection and skin samples are removed from IL-23-injected side and from the sterile saline-injected side, keeping at least 5 mm away from the hair boundary. Skin samples are frozen directly in liquid nitrogen for mRNA studies.

Total RNA is isolated from frozen skin tissue by homogenization in Lysing Matrix A shaker tubes (Qbiogene Inc./Bio101 Systems) followed by RNeasy Mini kit cleanup (Qiagen, Inc.). RNA concentrations are determined from spectrophotometric absorption at 260 nm. RNA is reverse-transcribed into cDNA using High-Capacity cDNA Reverse Transcription Kit (PE Applied Biosystems). All reactions are performed in triplicate on an ABI Prism 7900HT (PE Applied Biosystems) to determine the relative abundance of assayed mRNAs. Primer probe sets for mouse IL-17A (Mm00439618_m1), mouse IL-17F (Mm00521423_m1) and mouse keratin-16 (Mm00492979_g1) are obtained from PE Applied Biosystems. Both 18S and GAPD are measured as endogenous controls to normalize variability in gene expression levels. Expression data is analyzed using Delta (Δ-Δ) Ct method. Individual Ct values are calculated as means of triplicate measurements. Experiments are performed two times. Unpaired t-test is used where appropriate. P<0.05 is considered to be statistically significant.

To explore whether systemic administration of Antibody I is able to neutralize the local response to human IL-23, human IL-23 protein is injected intradermally into mice to investigate the downstream consequences of cutaneous IL-23 exposure. Skin from wild-type mice treated saline solution daily does not show detectable levels of mouse IL-17A or mouse IL-17F.

However, injection of human IL-23 induces mRNA expression of mouse IL-17A and mouse IL-17F (Table 5). Treatment with Antibody I but not isotype control antibody abrogated the human IL-23-induced IL-17A and IL-17F mRNA expression.

TABLE 5

In vivo neutralization of human IL-23 induced murine IL-17A and IL-17F mRNA expression.

| | Ct Values | | | |
|---|---|---|---|---|
| | PBS | | IL-23 | |
| | IL-17A | IL-17F | IL-17A | IL-17F |
| Isotype control | ≥40 | ≥40 | 35.4 | 31.6 |
| Antibody I | ≥40 | ≥40 | ≥40 | ≥40 |

Furthermore, human IL-23 injection induces an epidermal thickening associated with increased expression of keratin-16, a proliferation-associated cytokeratin. The induction of keratin-16 is significantly inhibited by administration of Antibody I (fold induction of murine keratin-16 is 5.21±2.72 for isotype control antibody versus 1.23±0.72 for Antibody I; p=0.0003).

All together, these results show that Antibody I effectively inhibits human IL-23-induced mouse IL-17A, IL-17F and keratin-16 mRNA production in an acute local in vivo assay.

Retinal Tissue Cross-Reactivity: In Vitro Analysis by Immunohistochemistry

Sections of fresh-frozen human and cynomolgus monkey retinal tissue (5-7 μm thick) are cut on a cryostat. The sections are fixed in acetone for approximately 10 minutes at room temperature, allowed to dry overnight at room temperature and stored at approximately −80° C. until use. Acetone-fixed slides are subsequently removed from the freezer and allowed to dry overnight at room temperature. The following steps are performed at room temperature. The slides are incubated in 1× Morphosave™ for approximately 15 minutes to preserve morphology. The slides are washed 10 minutes in 1×PBS and then incubated in 0.3% $H_2O_2$ in 1×PBS at room temperature for approximately 20 minutes to quench endogenous peroxidase activity. After incubation, the slides are washed two times for approximately 5 minutes in 1×PBS. Endogenous biotin is blocked by sequential incubation (approximately 15 minutes each) in avidin and biotin solutions. Following the incubation in biotin, the tissue sections are blocked with a blocking antibody solution for 30 minutes. Antibody I or control human $IgG_4$ is applied to sections at the optimal concentrations (2.5 or 5 μg/mL) or five times the optimal concentration (25 μg/mL) and incubated for 1 hour at room temperature. Slides are then rinsed and incubated with biotinylated mouse anti-human $IgG_4$ antibody (2.5 μg/mL) for 30 minutes. Bound primary/secondary antibody complexes are detected with streptavidin-biotin-horseradish peroxidase conjugate and a diaminobenzidine chromagen substrate.

CHO cells transfected with human IL-23 are used as a positive control sample in all experiments. Parental CHO (non-transfected) cells are used as a negative control sample and did not stain. Binding is not observed in serial sections stained with the isotype control antibody (human IgG4). Antibody I does not observably bind retinal tissue.

Epitope Mapping for Antibody I: Alanine Scanning

Background to Epitope Mapping Using Yeast Displayed Antigen

Epitope mapping studies are performed to determine the specific amino acids in the human IL-23 p19 subunit (SEQ ID NO: 15) that are required for Antibody I binding. Epitope mapping of Antibody I is completed by utilizing alanine scanning in conjunction with a yeast display platform.

Exposed amino acid positions of the p19 subunit of human IL-23 are identified by analysis in PyMOL. The exposed or partially exposed positions of the p19 subunit of IL-23 are shown in Table 6. Those positions that were determined not to be exposed are omitted from this study, i.e. only amino acid positions of the p19 subunit of human IL-23 that are exposed or partially exposed are mutated. Accordingly, not all positions are investigated.

Although the epitope mapping is only performed on the p19 subunit of IL-23 (no epitope mapping performed on the p40 subunit of IL-23 as Antibody I does not detectably bind to the p40 subunit), both the p19 subunit and p40 subunit of human IL-23 must be co-expressed in the yeast display platform.

Single yeast displayed alanine mutants of the p19 subunit of human IL-23 are constructed and antibody binding determined in order to identify the epitope. By measuring the affinity of antibody mutants compared to the wild-type yeast displayed antigen, it is possible to determine the energetic contribution of the amino acid side chain to antibody binding.

Mutant Library Construction

The p40 gene is cloned into the soluble-expression plasmid, pYKY, which has a uracil selection marker. The p19 subunit gene is cloned into the yeast display plasmid, pEMD3, which contains a tryptophan selection marker and a V5 tag at the N-terminus and to a GPDL2 anchor protein at the C-terminus allowing display on the surface of yeast under the tryptophan selectable marker. The restriction sites used for cloning are XhoI and BamHI in the pYKY plasmid and AvrII and XmaI in the pEMD3 plasmid, respectively.

Alanine mutations are introduced at every exposed position and tested for double positive staining with V5 antibody and Antibody I. Panels of p19 alanine mutants are constructed in pEMD3 plasmids using site directed mutagenesis (Kunkel Mutagenesis). Briefly, uracil containing ssDNA of the pEMD3 vector is produced after transformation into CJ236 (New England Biolabs). A single colony of the transformation is grown overnight and the ssDNA rescued following infection with M13K07 helper phage (New England Biolabs) and ssDNA purified using a QIAprep spin M13 kit. Oligonucleotides encoding alanine mutations are annealed at a 20:1 molar ratio to the uracil template by denaturing at 85° C. for 5 minutes, ramping to 55° C. over 1 hour, holding at 55° C. for 5 minutes, then chilling on ice. Second strand synthesis is then completed with T4 polymerase, T4 ligase and dNTPs (Invitrogen). The reaction is electroporated into Top10 *E. coli* (Invitrogen) and single colonies picked, dsDNA prepared using the QIAprep miniprep kit (Qiagen) and mutations confirmed by sequencing. p19 mutants are then co-transformed into BJ5464 yeast (ATCC) with the p40 pYKY plasmid and grown in complete minimal media without tryptophan and uracil.

Selection of Mutated Antigen Library for Loss of Antigen Binding

In order to identify the antibody epitope, the mutated antigen library is selected for loss of antibody binding by flow cytometry. Yeast cells are stained with two antibodies, one of which is being mapped and one of which is not. Yeast-displayed antigen mutants are selected for loss of binding to the first antibody, but retention of binding to the second antibody. Retention of binding of the second antibody ensures that mutants are selected on the basis of mutations in the epitope, rather than selection of unfolded or poorly displayed mutants.

For the present analysis, the first antibody (i.e. the antibody whose epitope is being mapped) is Antibody I and the second antibody is an anti-V5 antibody. Yeast are stained with anti-V5 antibody (Invitrogen) and Antibody I to begin with and subsequently with a secondary goat anti-mouse $IgG_{2a}$ (Invitrogen, Alexa Fluor® 647) to detect anti-V5 antibody (expression/display) and a goat anti-human kappa RPE (Southern Biotech) to detect Antibody I. Yeast are analyzed by flow cytometry on a Becton Dickinson LSRII, where 50,000 events are collected based on gating cells by light scatter, V5/Alexa647 and Antibody I/PE staining. Data analysis for binding of each of Antibody I and anti-V5 antibody is performed using FACSDiva v6.1.2 software, which calculates the percentage of double stained yeast cells.

Results

Due to displayed protein partition, at best 50% of yeast will display IL-23 p19. Detection of double-positive yeast cells demonstrate that the amino acid position under investigation is not involved with Antibody I binding to IL-23. Detection of only V5 staining demonstrates that the protein is expressed and displayed on the surface of the yeast and that the amino acid position under investigation is important for Antibody I binding. It is determined that those residues that demonstrated >50% reduction in double positive staining compared to adjacent residues are important for binding. These residues are highlighted in Table 7. Some positions demonstrate the lack of both V5 and Antibody I binding, suggesting that amino acid residue may be necessary for protein conformation. Systematic investigation of each exposed or partially exposed amino acid position in the IL-23 p19 subunit (SEQ ID NO: 15) demonstrates that positions 94P, 95S, 97L, 98P, 99D, 123W, 130S, 133P, and 137W are important for Antibody I binding to human IL-23 based on the reduced amount of double positive staining for V5 and Antibody I binding (Table 7).

Epitope mapping is also performed using hydrogen-deuterium exchange. The results of this hydrogen-deuterium exchange epitope mapping illustrate that the epitope of Antibody I is a conformational epitope within residues 81-99 and 115-140 of human IL-23 (SEQ ID NO: 15).

TABLE 6

Exposed or partially exposed amino acid sequence of mature human IL-23 p19 subunit

| | Position | | | | | | | | | |
|---|---|---|---|---|---|---|---|---|---|---|
| | 1 | 2 | 3 | 4 | 5 | 6 | 7 | 8 | 9 | 10 |
| Amino Acid | R | A | V | P | G | G | S | S | P | A |
| Exposed/Partially exposed | x | x | x | x | x | x | x | x | | x |

| | Position | | | | | | | | | |
|---|---|---|---|---|---|---|---|---|---|---|
| | 11 | 12 | 13 | 14 | 15 | 16 | 17 | 18 | 19 | 20 |
| Amino Acid | W | T | Q | C | Q | Q | L | S | Q | K |
| Exposed/Partially exposed | | x | x | | x | x | x | | x | x |

| | Position | | | | | | | | | |
|---|---|---|---|---|---|---|---|---|---|---|
| | 21 | 22 | 23 | 24 | 25 | 26 | 27 | 28 | 29 | 30 |
| Amino Acid | L | C | T | L | A | W | S | A | H | P |
| Exposed/Partially exposed | | | x | x | | | x | | x | x |

| | Position | | | | | | | | | |
|---|---|---|---|---|---|---|---|---|---|---|
| | 31 | 32 | 33 | 34 | 35 | 36 | 37 | 38 | 39 | 40 |
| Amino Acid | L | V | G | H | M | D | L | R | E | E |
| Exposed/Partially exposed | x | x | x | x | x | x | x | x | x | x |

| | Position | | | | | | | | | |
|---|---|---|---|---|---|---|---|---|---|---|
| | 41 | 42 | 43 | 44 | 45 | 46 | 47 | 48 | 49 | 50 |
| Amino Acid | G | D | E | E | T | T | N | D | V | P |
| Exposed/Partially exposed | x | x | x | x | x | x | x | x | | x |

| | Position | | | | | | | | | |
|---|---|---|---|---|---|---|---|---|---|---|
| | 51 | 52 | 53 | 54 | 55 | 56 | 57 | 58 | 59 | 60 |
| Amino Acid | H | I | Q | C | G | D | G | C | D | P |
| Exposed/Partially exposed | | | x | | x | x | x | | x | |

| | Position | | | | | | | | | |
|---|---|---|---|---|---|---|---|---|---|---|
| | 61 | 62 | 63 | 64 | 65 | 66 | 67 | 68 | 69 | 70 |
| Amino Acid | Q | G | L | R | D | N | S | Q | F | C |
| Exposed/Partially exposed | x | x | | x | x | x | | x | x | |

| | Position | | | | | | | | | |
|---|---|---|---|---|---|---|---|---|---|---|
| | 71 | 72 | 73 | 74 | 75 | 76 | 77 | 78 | 79 | 80 |
| Amino Acid | L | Q | R | I | H | Q | G | L | I | F |
| Exposed/Partially exposed | | x | x | | | x | | | x | x |

| | Position | | | | | | | | | |
|---|---|---|---|---|---|---|---|---|---|---|
| | 81 | 82 | 83 | 84 | 85 | 86 | 87 | 88 | 89 | 90 |
| Amino Acid | Y | E | K | L | L | G | S | D | I | F |
| Exposed/Partially exposed | | x | x | x | | x | x | x | | |

TABLE 6-continued

Exposed or partially exposed amino acid sequence of mature human IL-23 p19 subunit

| | Position | | | | | | | | | |
|---|---|---|---|---|---|---|---|---|---|---|
| | 91 | 92 | 93 | 94 | 95 | 96 | 97 | 98 | 99 | 100 |
| Amino Acid | T | G | E | P | S | L | L | P | D | S |
| Exposed/Partially exposed | x | x | x | x | x | x | x | x | x | x |

| | Position | | | | | | | | | |
|---|---|---|---|---|---|---|---|---|---|---|
| | 101 | 102 | 103 | 104 | 105 | 106 | 107 | 108 | 109 | 110 |
| Amino Acid | P | V | G | Q | L | H | A | S | L | L |
| Exposed/Partially exposed | | x | x | | x | x | x | | | x |

| | Position | | | | | | | | | |
|---|---|---|---|---|---|---|---|---|---|---|
| | 111 | 112 | 113 | 114 | 115 | 116 | 117 | 118 | 119 | 120 |
| Amino Acid | G | L | S | Q | L | L | Q | P | E | G |
| Exposed/Partially exposed | x | | | x | x | | x | | x | x |

| | Position | | | | | | | | | |
|---|---|---|---|---|---|---|---|---|---|---|
| | 121 | 122 | 123 | 124 | 125 | 126 | 127 | 128 | 129 | 130 |
| Amino Acid | H | H | W | E | T | Q | Q | I | P | S |
| Exposed/Partially exposed | x | x | | x | x | x | x | x | x | x |

| | Position | | | | | | | | | |
|---|---|---|---|---|---|---|---|---|---|---|
| | 131 | 132 | 133 | 134 | 135 | 136 | 137 | 138 | 139 | 140 |
| Amino Acid | L | S | P | S | Q | P | W | Q | R | L |
| Exposed/Partially exposed | x | x | x | x | x | x | x | x | x | x |

| | Position | | | | | | | | | |
|---|---|---|---|---|---|---|---|---|---|---|
| | 141 | 142 | 143 | 144 | 145 | 146 | 147 | 148 | 149 | 150 |
| Amino Acid | L | L | R | F | K | I | L | R | S | L |
| Exposed/Partially exposed | x | x | x | x | x | | | x | | |

| | Position | | | | | | | | | |
|---|---|---|---|---|---|---|---|---|---|---|
| | 151 | 152 | 153 | 154 | 155 | 156 | 157 | 158 | 159 | 160 |
| Amino Acid | Q | A | F | V | A | V | A | A | R | V |
| Exposed/Partially exposed | | | | | | | x | x | x | x |

| | Position | | | | | | | | | |
|---|---|---|---|---|---|---|---|---|---|---|
| | 161 | 162 | 163 | 164 | 165 | 166 | 167 | 168 | 169 | 170 |
| Amino Acid | F | A | H | G | A | A | T | L | S | P |
| Exposed/Partially exposed | x | x | x | x | x | x | x | x | x | x |

TABLE 7

Epitope Mapping Date for Antibody I

| Amino Acid Positions | % Double Positive Staining (V5 and Antibody I) |
|---|---|
| 87 | 26 |
| 88 | 27 |
| 91 | 37 |
| 92 | 29 |
| 94 | 16 |
| 95 | 12 |
| 96 | 35 |
| 97 | 7 |
| 98 | 10 |
| 99 | 7 |
| 100 | 22 |
| 118 | 31 |
| 119 | 28 |
| 120 | 26 |
| 121 | 28 |
| 122 | 31 |
| 123 | 5 |
| 124 | 26 |
| 125 | 18 |
| 126 | 22 |
| 127 | 25 |
| 129 | 21 |
| 130 | 4 |
| 133 | 1 |
| 134 | 16 |
| 136 | 15 |
| 137 | 2 |
| 140 | 23 |

Physical-Chemical Properties of IL-23 Antibody

Antibody I has pharmaceutically acceptable solubility, chemical stability and physical stability.

A. Solubility

Sufficiently high solubility is desired to enable convenient dosing. For example, a 1 mg/kg dose administered by a 1.0 mL injection into a 100 kg patient will require solubility of 100 mg/mL. In addition, maintaining the antibody in a monomeric state without high molecular weight (HMW) aggregation at high concentration is also desirable.

Antibody I is formulated at approximately 1 mg/mL in a physiological-like buffer (PBS, pH 7.4) and under two drug product formulation conditions (10 mM citrate, pH 6, plus and minus 150 mM NaCl). The antibody is centrifuged at 2000×G through an Amicon Ultra 30 kDa molecular weight filter (Millipore, UFC803204) to concentrate the antibody while maintaining the same buffer conditions. Centrifugation is continued until solubility limit or minimal holdup volume of the device is reached. Greater than 100 mg/mL solubility is achieved under all three conditions.

Size-exclusion chromatography (SEC) is used to assess whether an increase in high molecular weight (HMW) polymer occurred following concentration of the antibody formulations to greater than 100 mg/mL. The starting antibody solution and concentrated antibody solution are injected onto a TSK3000 SWXL column (TOSOH Bioscience) using a mobile phase consisting of 12 mM phosphate, 500 mM NaCl, pH 7.4. No large increase in soluble polymer is observed under any formulation condition tested (<0.6% HMW polymer by SEC).

B. Chemical Stability

Antibody I is formulated at 1 mg/mL in 10 mM buffer (10 mM citrate for pH 4, 5, 6, and 7; 10 mM TRIS for pH 8) and incubated for 4 weeks at 4, 25, or 40° C. Chemical stability is monitored by SEC (see above method), cation exchange chromatography [CEX; Dionex, using a gradient between Buffer A (20 mM sodium phosphate, pH 5.8, 0.36% CHAPS) and Buffer B (20 mM sodium phosphate, pH 5.8, 0.36% CHAPS, 200 mM sodium chloride)], CE-SDS (Agilent Bioanalyzer with a protein 230 chip under reducing conditions) and by LC-MS characterization of enzymatically digested material.

Antibody I is stable against polymer formation (SEC) over pH 5-8 even after 4-weeks at 40° C. At pH 4, significant polymer is observed at 40° C. but not at 25° C. (4 wk). Expected peptide bond hydrolysis or clipping is evident at pH 4 (40° C.) by CE-SDS. The degradation level at pH 4.0 is typical of $IgG_4$ antibodies. Above pH 4 (pH 5-8) levels are low and do not consistently change with time and thus likely represent background noise.

This hypothesis is consistent with the LC-MS analysis which detects no clipping at pH 6 while measuring typical level of antibody clipping at pH 4. Changes in charged variants are monitored by CEX. The starting material consists of three significant main peaks which minimize resolving power of this assay. In general, the 25° C. and 40° C. stressed samples are higher than the 4° C. control, but levels did not increase with incubation time (actually decreased in many cases). The percent change at pH 6.0 (4 wk at 25° C. minus 4° C. control) is 2.5%. LC-MS analysis indicates the majority of the modification is outside of the CDR region and is at levels typical of other IgG4 antibodies. Three degradation sites within the CDRs are identified changed less than 1% (pH 6; 4 wk at 25° C. minus 4° C. control). The lack of degradation sites within the CDRs is also consistent with no significant change in BIACore affinity or stoichiometry following four weeks at 40° C. incubation at either pH 4, 6, or 8.

C. Physical Stability i) Freeze Thaw Stability

Antibody I is formulated under the following conditions:

a) 1 mg/mL in 10 mM Citrate, pH 6.0;

b) 1 mg/mL in 10 mM Citrate, pH 6.0, 0.02% Tween-80;

c) 1 or 50 mg/mL in 10 mM Citrate, pH 6.0, 150 mM NaCl; and d) 1 or 50 mg/mL in 10 mM Citrate, pH 6.0, 150 mM NaCl, 0.02% Tween-80.

These formulations are placed in a 1° C./min controlled freezing container (Nalgene, 5100-0001) and frozen in a −80° C. freezer for at least eight hours and then removed and thawed at room temperature for at least eight hours. This freeze/thaw cycle is repeated up to three times. Samples are removed after one and three freeze thaw cycles and analyzed for HMW polymer by SEC (see SEC method described in part A above) and insoluble particle formation by HIAC particle counter (Pacific Scientific model 9703 with low volume attachment). No significant increase in HMW polymer formation is observed following three freeze thaw cycles under any conditions tested. For the 1 mg/ml formulations a significant increase in HIAC particle counts is observed only in the non-Tween-80 containing formulations. At 50 mg/ml particle counts were typical of other well performing IgG4 antibodies with particle counts (≥10 micron) were approximately 1500 counts/mL without Tween-80 and lowered to approximately 280 with Tween-80.

ii) Static Hold at High Concentration
Antibody is formulation at 50 mg/mL under the following conditions:
a) 10 mM Citrate, pH 6.0, 150 mM NaCl; and
b) 10 mM Citrate, pH 6.0, 150 mM NaCl, 0.02% Tween-80

These formulations are held static for 4-weeks at 4 and 25° C. The change in HIAC particle counts (Pacific Scientific model 9703 with low volume attachment) is measured after 4-weeks at 25° C.

HIAC particle counts (≥10 micron) for Tween containing formulations average 290 counts/mL (270 and 310) and moderately higher, 804 counts/mL (728 and 880) for formulations without Tween. These results are typical of other IgG4 antibodies that exhibit good physical stability. These two formulations were also stored in glass instead of standard plastic eppendorf tubes. Particle counts for the samples stored in glass are 4 to 8 fold lower (average 35 and 191 counts/mL respective for with and without Tween).

SEQ ID Listing

Heavy Chain CDRs

SEQ ID NO: 1
GYKFTRYVMH

SEQ ID NO: 2
YINPYNDGTNYNEKFKG

SEQ ID NO: 3
ARNWDTGL

Light Chain CDRs

SEQ ID NO: 4
KASDHILKFLT

SEQ ID NO: 5
GATSLET

SEQ ID NO: 6
QMYWSTPFT

Heavy Chain Variable Regions (Antibody I)
SEQ ID NO: 7
QVQLVQSGAEVKKPGSSVKVSCKASGYKFTRYVMHWVRQAPGQGLEWMGYINPYNDGTNYNEKFKG
RVTITADKSTSTAYMELSSLRSEDTAVYYCARNWDTGLWGQGTTVTVSS

Light Chain Variable Regions (Antibody I)
SEQ ID NO: 8
DIQMTQSPSSLSASVGDRVTITCKASDHILKFLTWYQQKPGKAPKLLIYGATSLETGVPSRFSGSG
SGTDFTLTISSLQPEDFATYYCQMYWSTPFTFGGGTKVEIK

Complete Heavy Chain (Antibody I)
SEQ ID NO: 9
QVQLVQSGAEVKKPGSSVKVSCKASGYKFTRYVMHWVRQAPGQGLEWMGYINPYNDGTNYNEKFKG
RVTITADKSTSTAYMELSSLRSEDTAVYYCARNWDTGLWGQGTTVTVSSASTKGPSVFPLAPCSRS
TSESTAALGCLVKDYFPEPVTVSWNSGALTSGVHTFPAVLQSSGLYSLSSVVTVPSSSLGTKTYTC
NVDHKPSNTKVDKRVESKYGPPCPPCPAPEAAGGPSVFLFPPKPKDTLMISRTPEVTCVVVDVSQE
DPEVQFNWYVDGVEVHNAKTKPREEQFNSTYRVVSVLTVLHQDWLNGKEYKCKVSNKGLPSSIEKT
ISKAKGQPREPQVYTLPPSQEEMTKNQVSLTCLVKGFYPSDIAVEWESNGQPENNYKTTPPVLDSD
GSFFLYSRLTVDKSRWQEGNVFSCSVMHEALHNHYTQKSLSLSLG

Complete Light Chain (Antibody I)
SEQ ID NO: 10
DIQMTQSPSSLSASVGDRVTITCKASDHILKFLTWYQQKPGKAPKLLIYGATSLETGVPSRFSGSG
SGTDFTLTISSLQPEDFATYYCQMYWSTPFTFGGGTKVEIKRTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC

Nucleotide Sequences

Heavy Chain Variable Region
(Antibody I)
SEQ ID NO: 11
CAGGTGCAGCTGGTGCAGTCTGGGGCTGAGGTGAAGAAGCCTGGGTCCTCGGTGAAGGTCTCCTGC
AAGGCTTCTGGATATAAATTCACTCGTTATGTTATGCACTGGGTGCGACAGGCCCCTGGACAAGGG
CTTGAGTGGATGGGATATATTAATCCTTACAATGATGGTACTAACTACAATGAGAAGTTCAAAGGC
AGAGTCACGATTACCGCGGACAAATCCACGAGCACAGCCTACATGGAGCTGAGCAGCCTGAGATCT

```
GAGGACACGGCCGTGTATTACTGTGCGAGAAACTGGGACACAGGCCTCTGGGGCCAAGGCACCACT
GTCACAGTCTCCTCA
```

Nucleotide Sequences

Light Chain Variable Regions
(Antibody I)
SEQ ID NO: 12
```
GACATCCAGATGACCCAGTCTCCATCCTCCTGTCTGCATCTGTAGGAGACAGAGTCACCATCACT
TGCAAGGCAAGTGACCACATTCTCAAATTTTTAACTTGGTATCAGCAGAAACCAGGGAAAGCCCCT
AAGCTCCTGATCTATGGTGCAACCAGTTTGGAAACTGGGGTCCCATCAAGGTTCAGTGGCAGTGGA
TCTGGGACAGATTTCACTCTCACCATCAGCAGTCTGCAACCTGAAGATTTTGCAACTTACTACTGT
CAAATGTATTGGAGTACTCCGTTCACGTTCGGAGGGGGGACCAAGGTGGAAATAAAA
```

Nucleotide Sequence

Complete Heavy Chain
(Antibody I)
SEQ ID NO: 13
```
CAGGTGCAGCTGGTGCAGTCTGGGGCTGAGGTGAAGAAGCCTGGGTCCTCGGTGAAGGTCTCCTGC
AAGGCTTCTGGATATAAATTCACTCGTTATGTTATGCACTGGGTGCGACAGGCCCCTGGACAAGGG
CTTGAGTGGATGGGATATATTAATCCTTACAATGATGGTACTAACTACAATGAGAAGTTCAAAGGC
AGAGTCACGATTACCGCGGACAAATCCACGAGCACAGCCTACATGGAGCTGAGCAGCCTGAGATCT
GAGGACACGGCCGTGTATTACTGTGCGAGAAACTGGGACACAGGCCTCTGGGGCCAAGGCACCACT
GTCACAGTCTCCTCAGCCTCCACCAAGGGCCCATCGGTCTTCCCGCTAGCGCCCTGCTCCAGGAGC
ACCTCCGAGAGCACAGCCGCCCTGGGCTGCCTGGTCAAGGACTACTTCCCCGAACCGGTGACGGTG
TCGTGGAACTCAGGCGCCCTGACCAGCGGCGTGCACACCTTCCCGGCTGTCCTACAGTCCTCAGGA
CTCTACTCCCTCAGCAGCGTGGTGACCGTGCCCTCCAGCAGCTTGGGCACGAAGACCTACACCTGC
AACGTAGATCACAAGCCCAGCAACACCAAGGTGGACAAGAGAGTTGAGTCCAAATATGGTCCCCCA
TGCCCACCCTGCCCAGCACCTGAGGCCGCCGGGGGACCATCAGTCTTCCTGTTCCCCCCAAAACCC
AAGGACACTCTCATGATCTCCCGGACCCCTGAGGTCACGTGCGTGGTGGTGGACGTGAGCCAGGAA
GACCCCGAGGTCCAGTTCAACTGGTACGTGGATGGCGTGGAGGTGCATAATGCCAAGACAAAGCCG
CGGGAGGAGCAGTTCAACAGCACGTACCGTGTGGTCAGCGTCCTCACCGTCCTGCACCAGGACTGG
CTGAACGGCAAGGAGTACAAGTGCAAGGTCTCCAACAAAGGCCTCCCGTCCTCCATCGAGAAAACC
ATCTCCAAAGCCAAAGGGCAGCCCCGAGAGCCACAGGTGTACACCCTGCCCCCATCCCAGGAGGAG
ATGACCAAGAACCAGGTCAGCCTGACCTGCCTGGTCAAAGGCTTCTACCCCAGCGACATCGCCGTG
GAGTGGGAAAGCAATGGGCAGCCGGAGAACAACTACAAGACCACGCCTCCCGTGCTGGACTCCGAC
GGCTCCTTCTTCCTCTACAGCAGGCTAACCGTGGACAAGAGCAGGTGGCAGGAGGGGAATGTCTTC
TCATGCTCCGTGATGCATGAGGCTCTGCACAACCACTACACACAGAAGAGCCTCTCCCTGTCTCTG
GGT
```

Nucleotide Sequence

Complete Light Chain
(Antibody I)
SEQ ID NO: 14
```
GACATCCAGATGACCCAGTCTCCATCCTCCTGTCTGCATCTGTAGGAGACAGAGTCACCATCACT
TGCAAGGCAAGTGACCACATTCTCAAATTTTTAACTTGGTATCAGCAGAAACCAGGGAAAGCCCCT
AAGCTCCTGATCTATGGTGCAACCAGTTTGGAAACTGGGGTCCCATCAAGGTTCAGTGGCAGTGGA
TCTGGGACAGATTTCACTCTCACCATCAGCAGTCTGCAACCTGAAGATTTTGCAACTTACTACTGT
CAAATGTATTGGAGTACTCCGTTCACGTTCGGAGGGGGGACCAAGGTGGAAATAAAACGAACTGTG
GCTGCACCATCTGTCTTCATCTTCCCGCCATCTGATGAGCAGTTGAAATCTGGAACTGCCTCTGTT
GTGTGCCTGCTGAATAACTTCTATCCCAGAGAGGCCAAAGTACAGTGGAAGGTGGATAACGCCCTC
CAATCGGGTAACTCCCAGGAGAGTGTCACAGAGCAGGACAGCAAGGACAGCACCTACAGCCTCAGC
AGCACCCTGACGCTGAGCAAAGCAGACTACGAGAAACACAAAGTCTACGCCTGCGAAGTCACCCAT
CAGGGCCTGAGCTCGCCCGTCACAAAGAGCTTCAACAGGGGAGAGTGC
```

Protein Sequences

Mature Human IL-23 p19 subunit amino acid sequence
SEQ ID NO: 15
```
RAVPGGSSPAWTQCQQLSQKLCTLAWSAHPLVGHMDLREEGDEETTNDVPHIQCGDGCDPQGLRDN
SQFCLQRIHQGLIFYEKLLGSDIFTGEPSLLPDSPVQLHASLLGLSQLLQPEGHHWETQQIPSLS
PSQPWQRLLLRFKILRSLQAFVAVAARVFAHGAATLSP
```

---

The invention claimed is:

1. A DNA molecule comprising a polynucleotide sequence encoding an antibody light chain polypeptide having the amino acid sequence SEQ ID NO: 10.

2. A DNA molecule comprising a polynucleotide sequence encoding an antibody heavy chain polypeptide having the amino acid sequence SEQ ID NO: 9.

3. A recombinant host cell comprising a DNA molecule comprising a polynucleotide sequence encoding a light chain polypeptide having the amino acid sequence SEQ ID NO: 10 and a DNA molecule comprising a polynucleotide sequence encoding a heavy chain polypeptide having the amino acid sequence SEQ ID NO: 9, which cell is capable of expressing an antibody comprising a heavy chain and a light chain, wherein the amino acid sequence of the heavy chain is SEQ ID NO: 9 and the amino acid sequence of the light chain is SEQ ID NO: 10.

4. A process for producing an antibody that binds to the p19 subunit of human IL-23 and comprises a heavy chain and a light chain, wherein the heavy chain comprises the amino acid sequence of SEQ ID NO:9 and the light chain comprises the amino acid sequence of SEQ ID NO: 10, said process comprising the steps of:

a) cultivating a recombinant host cell of claim 3, under conditions such that said antibody is expressed; and b) recovering from said host cell the expressed antibody.

5. An antibody produced by the process of claim 4.

6. A pharmaceutical composition comprising the antibody of claim 5 and one or more pharmaceutically acceptable carriers, diluents or excipients.

\* \* \* \* \*

UNITED STATES PATENT AND TRADEMARK OFFICE
CERTIFICATE OF CORRECTION

PATENT NO. : 9,688,753 B2  
APPLICATION NO. : 14/702124  
DATED : June 27, 2017  
INVENTOR(S) : Catherine Brautigam Beidler et al.

Page 1 of 1

It is certified that error appears in the above-identified patent and that said Letters Patent is hereby corrected as shown below:

On the Title Page

Item (54) and in the Specification, (Lines 1 and 2) the Title should reflect "ANTIBODIES THAT BIND IL-23".

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*